United States Patent [19]

Winchell et al.

[11] Patent Number: 5,011,477

[45] Date of Patent: Apr. 30, 1991

[54] CONTINUOUS/BOLUS INFUSOR

[75] Inventors: David A. Winchell, Spring Grove; James L. Sertic, Grayslake, both of Ill.

[73] Assignee: Baxter International Inc., Deerfield, Ill.

[21] Appl. No.: 341,527

[22] Filed: Apr. 21, 1989

[51] Int. Cl.$^5$ .................................. A61M 37/00
[52] U.S. Cl. ...................... 604/132; 604/151; 604/246; 120/DIG. 12
[58] Field of Search ...................... 604/131–132, 604/151–153, 246, 183, 185, 186, 891, 52.53; 120/DIG. 12

[56] References Cited

U.S. PATENT DOCUMENTS

| | | | |
|---|---|---|---|
| D. 237,113 | 10/1975 | Hoff et al. | D83/1 F |
| 2,471,623 | 5/1949 | Hubbell | 251/5 |
| 3,468,308 | 9/1969 | Bierman | 128/214 |
| 3,469,578 | 9/1969 | Bierman | 128/214 |
| 3,486,539 | 12/1969 | Jacuzzi | 141/329 |
| 3,698,595 | 10/1972 | Gortz et al. | 220/63 |
| 3,767,078 | 10/1973 | Gortz et al. | 220/63 |
| 3,831,600 | 8/1974 | Yum et al. | 128/214 |
| 3,895,631 | 7/1975 | Buckles et al. | 128/213 |
| 3,907,169 | 9/1975 | Gortz et al. | 222/95 |
| 3,993,069 | 11/1976 | Buckles et al. | 128/214 |
| 4,121,584 | 10/1978 | Turner et al. | 128/214 |
| 4,140,117 | 2/1979 | Buckles et al. | 128/213 |
| 4,201,207 | 5/1980 | Buckles et al. | 128/214 |
| 4,209,014 | 6/1980 | Sefton | 604/132 |
| 4,215,689 | 8/1980 | Akiyama et al. | 128/214 |
| 4,318,400 | 3/1982 | Peery et al. | 128/214 |
| 4,337,769 | 7/1982 | Olson | 128/214 |
| 4,381,006 | 4/1983 | Genese | 128/218 |
| 4,386,929 | 6/1983 | Peery et al. | 604/132 |
| 4,398,908 | 8/1983 | Siposs | 604/31 |
| 4,419,096 | 12/1983 | Leeper et al. | 604/132 |
| 4,447,232 | 5/1984 | Sealfon et al. | 604/134 |
| 4,537,680 | 8/1985 | Barth | 210/316 |
| 4,544,371 | 10/1985 | Dormandy, Jr. et al. | 604/891 |
| 4,548,599 | 10/1985 | Urguhart et al. | 604/246 |
| 4,548,607 | 10/1985 | Harris | 604/891 |
| 4,551,133 | 11/1985 | de Beyl et al. | 604/66 |
| 4,559,038 | 12/1985 | Berg et al. | 604/153 |
| 4,588,394 | 5/1986 | Schulte et al. | 604/9 |
| 4,597,758 | 7/1986 | Aalto et al. | 604/256 |
| 4,601,707 | 7/1986 | Albisser et al. | 604/131 |
| 4,626,244 | 12/1986 | Reinicke | 604/141 |
| 4,634,427 | 1/1987 | Hannula et al. | 604/93 |
| 4,668,231 | 5/1987 | de Vries et al. | 604/891 |
| 4,681,560 | 7/1987 | Schulte et al. | 604/9 |
| 4,699,615 | 10/1987 | Fishell et al. | 604/131 |
| 4,702,397 | 10/1987 | Gortz | 222/211 |
| 4,741,733 | 5/1988 | Winchell et al. | 604/51 |
| 4,769,008 | 9/1988 | Hessel | 604/132 |
| 4,822,344 | 4/1989 | O'Boyle | 604/246 |
| 4,828,551 | 5/1989 | Gertler et al. | 604/208 |
| 4,898,584 | 2/1990 | Borsanyi et al. | 604/153 |
| 4,898,585 | 2/1990 | Borsanyi et al. | 604/153 |
| 4,954,129 | 9/1990 | Guliani et al. | 604/131 |

FOREIGN PATENT DOCUMENTS

| | | | |
|---|---|---|---|
| 0168675 | 1/1986 | European Pat. Off. | |
| 82/04399 | 12/1982 | PCT Int'l Appl. | |
| 86/03978 | 7/1986 | PCT Int'l Appl. | 604/132 |
| 87/00758 | 2/1987 | PCT Int'l Appl. | 604/132 |

OTHER PUBLICATIONS

Jane W. Kwon, "High-Technology I.V. Infusion Devices", American Journal of Hospital Pharmacy, vol. 46, Feb. 1989, pp. 320–335.

Primary Examiner—C. Fred Rosenbaum
Assistant Examiner—Kathleen A. Daley
Attorney, Agent, or Firm—Paul E. Schaafsma; Bradford R. L. Price; Paul C. Flattery

[57] ABSTRACT

The present invention provides both a continuous dose and a bolus dose of fluid or beneficial agent to a patient. A source of fluid is in fluid communication with a continuous flow path for providing the patient with a continuous source of the beneficial agent. The source of beneficial agent is also connected to a bolus dose apparatus which provides patient control of a bolus dose of the beneficial agent, up to a preselected maximum.

15 Claims, 4 Drawing Sheets 5,011,477

CONTINUOUS/BOLUS INFUSOR

FIELD OF THE INVENTION

The present invention relates to the controlled delivery of fluids and, in particular, to a system and apparatus for the delivery of a preselected quantity of a beneficial agent to a patient.

BACKGROUND OF THE INVENTION

The controlled delivery of a preselected quantity of a beneficial agent to a patient is highly desirable in a number of situations. Particularly, the controlled delivery of drugs such as analgesics is highly desirable as there is great difficulty in properly administering analgesics. The need to administer analgesics varies greatly from patient to patient. Such factors as, for example, age, pain tolerance, renal function, and presence of other medications can all affect the pharmacokinetics of such analgesic.

In the area of analgesic administration, there has been much activity in the last several years directed towards letting the patient control how much drug he or she administers. It has been found that, as a group, patients controlling the quantity they receive use less analgesic than patients who must request the administration of a pain killer. One apparent factor is the psychological relief present when a patient knows he or she is in control of the amount of drug to be administered. The amount of drug the patient can self-administer must also be subject to a maximum level of drug.

The efficient patient controlled administration of drug has resulted in several devices on the market. Such devices generally suffer from several drawbacks. Initially, such devices are electromechanical in nature thus requiring an electrical power source. In addition, such devices are large and bulky which limits the patient's freedom to move.

Another drawback of such devices is that they only provide an on-demand rush of the drug as administered by the patient with no constant drug flow to the patient. While this type of drug administration is appropriate for many situations, it is often desirable to have a constant flow of drug to the patient, referred to herein as a continuous flow, supplemented by a patient controlled supplement of drug, referred to herein as a bolus flow. While several devices on the market are designed to provide such continuous flow supplemented by a patient controlled flow, such devices are again electromechanical in nature and are large and bulky thus limiting the patients' ability to move.

While, of course, two separate devices can be utilized to provide this continuous-bolus flow arrangement, such use of two devices adds to the cost and complexity of the system while further limiting patient mobility. What is thus needed is an apparatus and system for both a constant delivery of a beneficial agent and a patient controlled supplement of the beneficial agent which is low in cost, highly mobile, and easy to use. The present device meets these requirements.

SUMMARY OF THE INVENTION

The present invention includes means for providing a source of fluid which includes the beneficial agent under pressure which in the preferred embodiment in an elastomeric bladder. Means for regulating a constant flow rate of the beneficial agent are provided in fluid communication with the source of fluid. In a preferred embodiment, the regulator means includes a flow regulator.

Bolus dose means for providing a patient controlled bolus dose of the beneficial agent are also provided in fluid communication with the source of fluid. The preferred bolus dose means includes a dose reservoir in fluid communication with the source of fluid under pressure and downstream tubing, and control means for expressing the fluid in the dose reservoir from the dose reservoir to the downstream tubing. A flow regulator can be provided which regulates the flow a fluid to the dose reservoir at a constant flow rate and the dose reservoir can have an upper volume limit which represents the discrete dose limit of the apparatus.

DETAILED DESCRIPTION OF A PREFERRED EMBODIMENT

Figure 1:
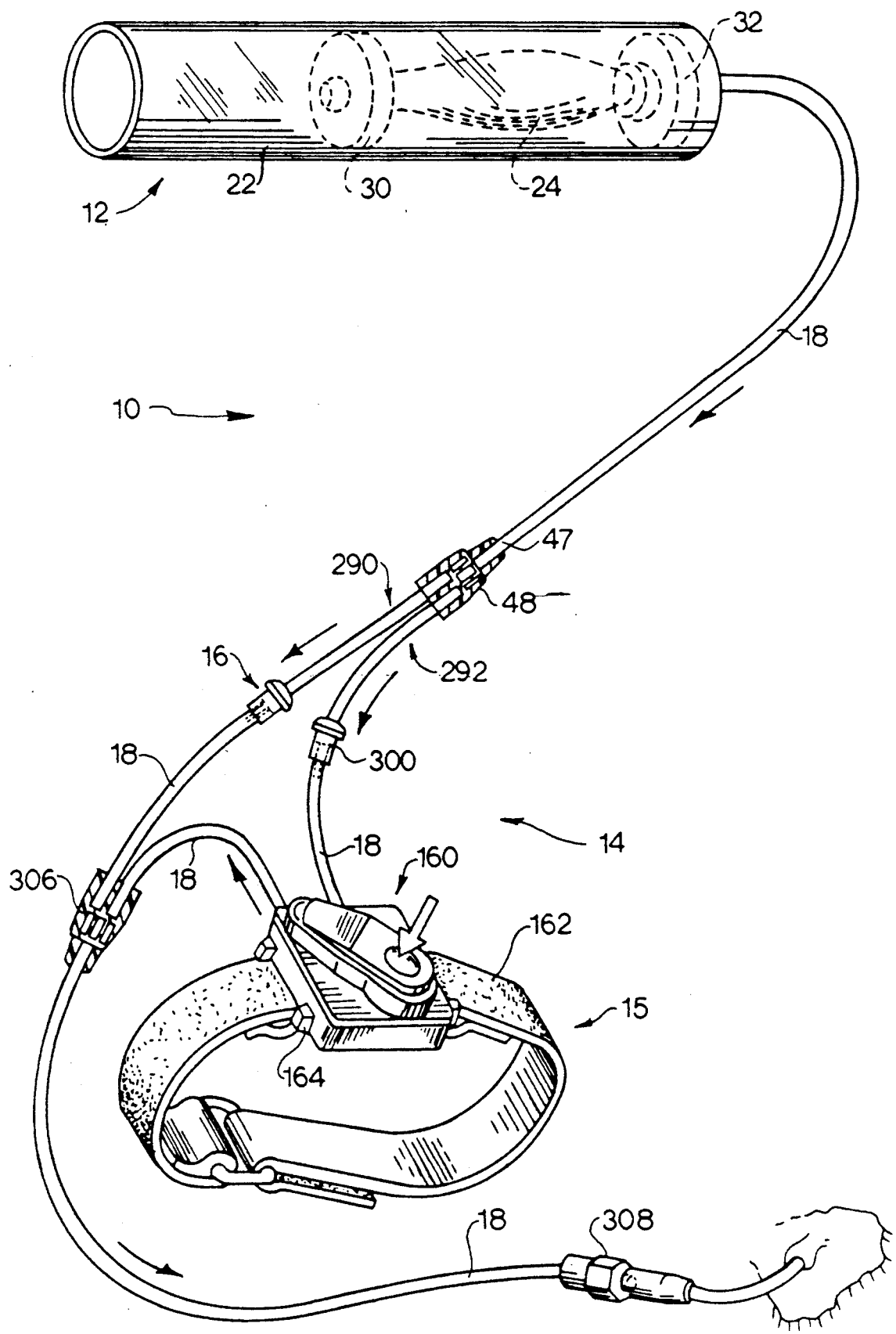
FIG. 1 is a perspective view of a preferred embodiment of a device made in accord with the principles of the present invention.

Referring first to FIG. 1, a completed assembly in accord with the present invention is designated generally by the reference numeral 10. The completed device generally includes means for providing a source of fluid under pressure 12, bolus dose means for providing a controlled bolus dose of the fluid 14, and means for regulating a constant flow rate of fluid 16. Each means is in fluid communication by means such as flexible tubing 18 made of medical grade plastic such as, for example, polyvinyl chloride. Each tube segment connecting the various means acts as both a downstream conduit and an upstream conduit for the two means being connected. For example, the tubing segment 18 between the means for providing a source of fluid 12 and the controlled bolus dose means 14 acts as a downstream conduit for the fluid source means 12 as well as an upstream conduit for the bolus dose means 14.

Figure 2:
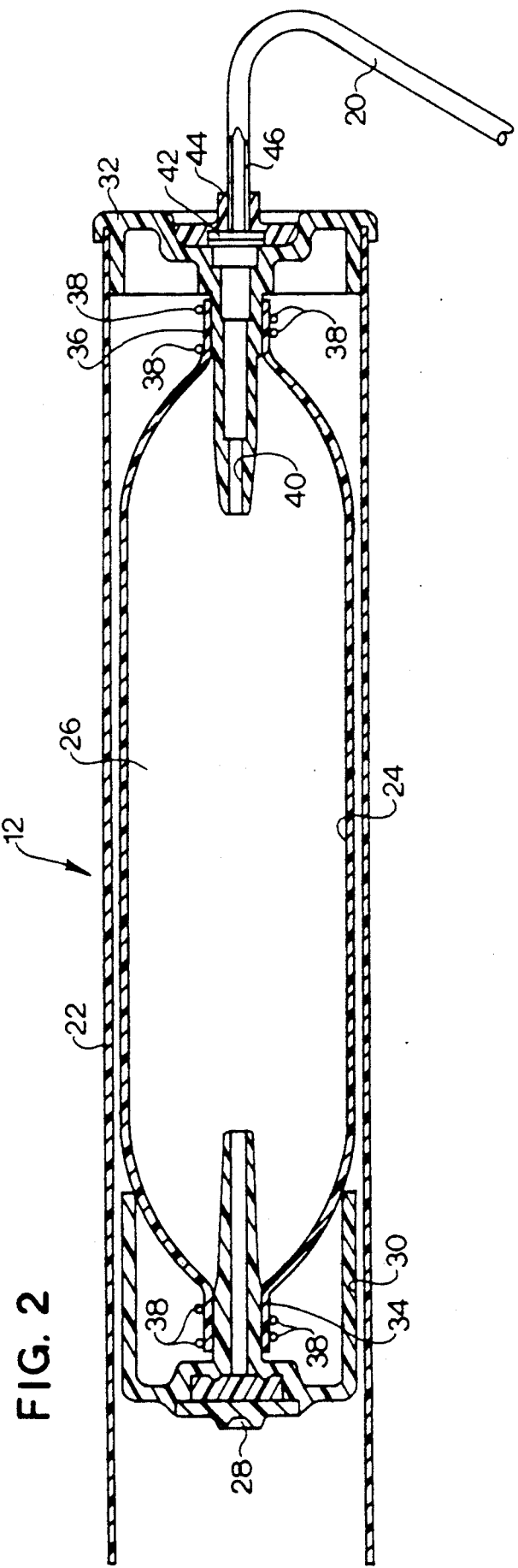
FIG. 2 is a cross-sectional view of the means for providing a source of fluid under pressure of the device of FIG. 1.

Referring now to FIG. 2, a preferred embodiment of the means for providing a source of fluid under pressure 12 is seen. The presently preferred means is a device such as the Infusor sold by Baxter Healthcare Corporation (formerly Travenol Laboratories) of Deerfield, Ill. and shown in U.S. Pat. No. 4,741,733 to Winchell et al, which is assigned to the assignee of the present invention and which disclosure is incorporated herein.

Such device includes a tubular housing 22. An elastomeric bladder 24 which is contained in the tubular housing 22 contains the fluid or beneficial agent 26 which is to be delivered.

The elastomeric bladder 24 of the assembly is self pressurized; that is, as a liquid such as the beneficial agent 26 is injected through means for receiving liquid under pressure, the elastomeric bladder 24 expands. The elastomeric bladder 24 exerts a substantially constant pressure on the fluid 26 throughout the volume range of the elastomeric bladder 24. The pressure within bladder 24 on the fluid 26 therein can preferably be about eight PSI.

The bladder 24 is secured at a free end 34 to a floating piston 30. The floating piston 30 includes the means for receiving a liquid under pressure 28 so that the expandable bladder 24 can be filled. Such means can include a one-way valve contained in the housing having threaded receiving means for receiving a syringe absent a hypodermic needle for providing the fluid under pressure. Such means can alternately include a rubber membrane through which a syringe having a hypodermic needle can pierce to provide the fluid under pressure.

The bladder 24 is secured at a fixed end 36 to a plug 32 which is mounted to the housing 22. The plug 32 may be unitary with the housing 22. The free end 34 and fixed end 36 may be secured to the floating piston 30 and plug 32, respectively, by means of wire clamps 38, banding or the like. As fluid 26 is expressed from the expanded bladder 24, the floating piston 30 moves toward the plug 32. The plug 32 includes an aperture 40 extending therethrough which is in fluid communication with the inside of bladder 24.

A filter element 42 such as a polyester screen filter can be mounted across the aperture 40 to filter fluid 26 flowing out of bladder 24. The plug 32 may include an end piece 44 secured to the plug 32 by, for example, sonic welding to mount the filter element 42 within plug 32 and to secure the first segment tubing 18 to plug 32.

The tubing 18 includes a proximal end 46 and a distal end 47. The tubing proximal end 46 is secured to the end piece 44 of plug 32 by, for example, adhesive or the like. The distal end 47 is secured to a Y-connector 48, as will be explained in more detail below.

Referring now back to FIG. 1, the means for regulating a constant flow rate of the fluid 16 and the bolus dose means for providing a controlled bolus dose of the fluid 14 are seen. The means for regulating a constant flow rate of the fluid 16 is in fluid communications with the means for providing a source of fluid under pressure 12 via the tubing 18.

Figure 3:
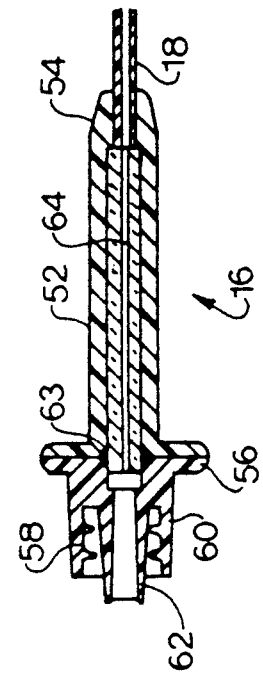
FIG. 3 is a cross-sectional view of a preferred embodiment of the flow regulator means of the device of FIG. 1.

Referring now to FIG. 3, a preferred embodiment of the flow regulator means 16 of the present invention is seen. Such flow regulator means is also shown in U.S. Pat. No. 4,741,733 to Winchell et al. The flow regulator means 16 includes regulator housing 52 having a flow regulator 64 dispensed therein. The regulator housing 52 is secured at an inlet passage 54 to tubing 18 extending from the Y-connector 48 by, for example, solvent bonding about the outside diameter of tubing 18.

Opposite the inlet passage 54, the regulator housing 52 includes an enlarged outlet passage 56 forming an annular flange with and being connected to an internally threaded sleeve 58 of a locking Luer 60. The Luer lock 60 includes a Luer taper element 62 which is adapted for connection with a female Luer contained on a downstream tube segment.

A sealing element such as an O-ring 63 is disposed around the periphery of flow regulator 64 to prevent fluid from flowing between the outside of regulator 64 and regulator housing 52. The O-ring 63 is mounted in an annular channel around the periphery of flow regulator 64. The channel has a triangular cross section. The three sides of the channel are formed by the flow regulator 64, a beveled corner of the enlarged end of housing 52 and the threaded sleeve 58 of the connecting means.

The O-ring 63 is pressed within and conforms to the shape of the channel as the channel is formed. The channel is formed when the threaded sleeve 56 and the enlarged end of housing 52 are secured together by means such as, for example, sonic welding. The pressure placed on the sealing element 64 by the threaded sleeve 58 and the enlarged end of housing 52 deforms the O-ring 62 substantially into the shape of the channel thereby effectively sealing the flow regulator 64 and the housing 52. Thus, different length flow regulators 64 can be utilized in the housing 52.

In a preferred embodiment, the flow regulator 64 includes a capillary-type flow restrictor. One such capillary-type flow restrictor can be made of glass which defines a very small bore in fluid communication with the tubing.

The fluid flow rate through the tubing 18 is determined by the characteristics of the capillary-type flow restrictor along with the characteristics of the fluid which flows through the flow restrictor. In a glass bore flow restrictor, the flow rate can be changed by varying the cross-sectional area and length of the regulator bore.

Figure 4:
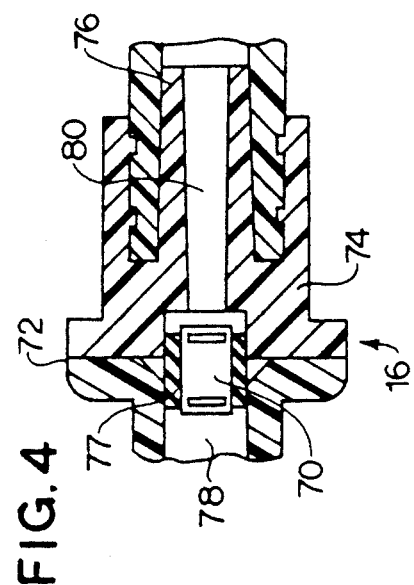
FIG. 4 is a cross-sectional view of an alternative preferred embodiment of the flow regulator means.

In a second preferred embodiment, the flow regulator includes a flow restrictor chip or wafer encapsulated in housing. Such a device is shown in U.S. application Ser. No. 167,822 to Winchell et al. which is assigned to the assignee of the present invention which disclosure is incorporated herein. Referring to FIG. 4, this alternative preferred embodiment is seen in detail.

The flow restrictor chip 70 is contained in housing 72 which includes a locking Luer 74 contained at the end of tubing. The Luer lock 74 includes a Luer taper element 76 adapted for connection with a female Luer contained on downstream tubing.

A seal member 77 is located between an inlet passage 78 and an outlet passage 80. The wafer or chip 70 is carried within seal member 77 with the wafer 70 having an inlet in fluid communication with the inlet passage 78 and the wafer 70 having an outlet in fluid communication with the outlet passage 80. All fluid traversing the housing 72 must pass through the flow restrictor path of wafer or chip 70. The wafer or chip 70 thus serves to regulate the flow rate of the fluid.

Figure 5:
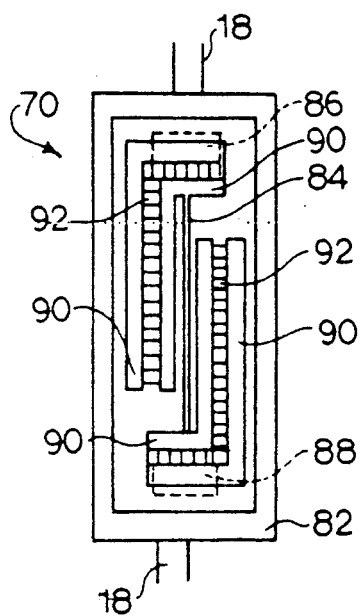
FIG. 5 is an enlarged overview of a preferred embodiment of the flow rate wafer of FIG. 4.

Referring now to FIG. 5, a preferred embodiment of the wafer or chip 70 is seen in detail. The wafer 70 includes a base substrate 82 into which one or more flow restrictor paths 84 are formed. These paths can be of various geometrics such as V-shaped, arcuately shaped or rectangularly shaped; depending on the nature of the substrate and the etching technique utilized. In the illustrated embodiment, a single main flow restrictor path 84 is formed having a preselected discrete resistance to fluid flow.

The path may be enclosed by various means such as an overlay (not seen) covering the base substrate 82 to enclose the restrictor path 84. The inlet 86 and outlet 88 of wafer 70 are formed as apertures in base substrate 82 which form fluid communication paths at opposite ends of flow restrictor path 84.

Manifold regions 90 can also preferably be preformed on the base substrate 82 at opposite ends of flow restrictor path 84 to assure a non-restricted flow on the wafer 70. Also, a plurality of secondary flow restrictor paths 92, with each secondary flow restrictor path 92 smaller than the main flow restrictor path 84, can be provided to filter out small particulate matter during passage across the wafer 70.

Figure 6:
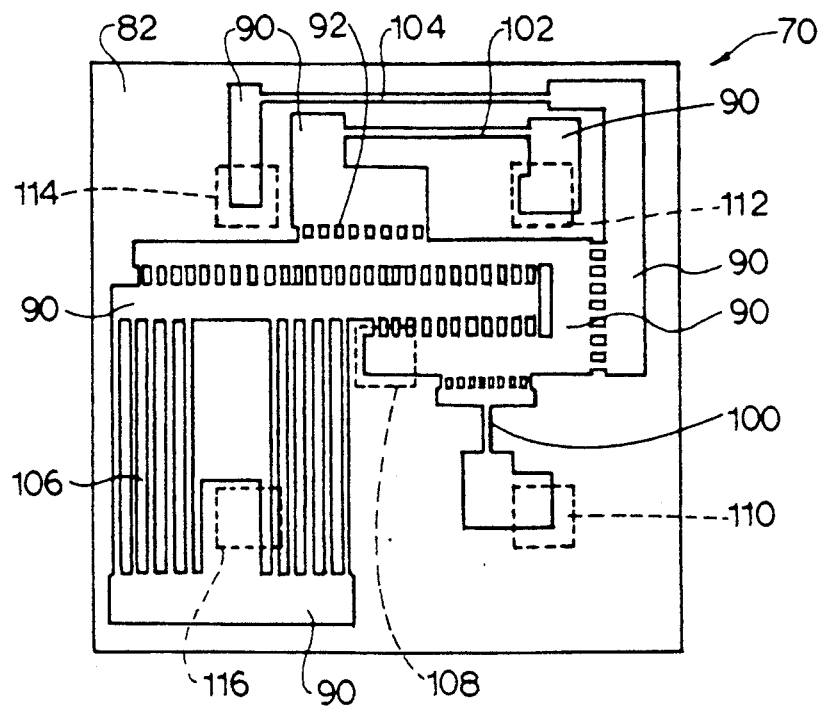
FIG. 6 is an enlarged overview of an alternative preferred embodiment of the flow rate wafer.

In an alternative embodiment of the presently preferred flow control means 14, a wafer or chip 70 having at least two independent flow restrictor paths formed on the base substrate can be utilized. Such a wafer is seen in FIG. 6 in which four flow restrictor paths are seen.

In this embodiment, the four restrictor paths 100, 102, 104, 106 are formed between a Central wafer inlet 108 and first 110, second 112, third 114 and fourth 116 restrictor outlets. Each path is formed with a preselected cross sectional area and length to provide a different resistance to flow. Fluid transversing each flow restrictor path will therefore flow at a different, preselected flow rate.

The wafer again includes fluid manifolds 90 formed in association with each flow restrictor path 100, 102, 104, 106. In addition, filtration areas 92 can also once again be formed.

Figure 7:
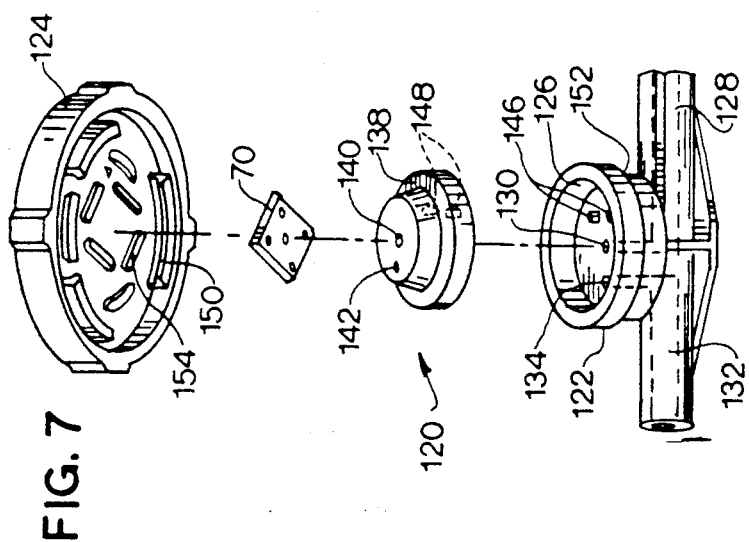
FIG. 7 is an exploded perspective view of the selector housing for the flow rate wafer of FIG. 6.

The multi-path flow restrictor chip is contained in selector housing 120. Referring to FIG. 7, the selector housing 120 is seen in detail. The selector housing 120 includes a base member 122 and a selector member 124 which is normally carried on the base member 122. The base member 122 includes a well 126. An inlet passage 128 communicates with the well 126 by means of an inlet port 130. An outlet passage 132 also communicates with the well 126 by means of an outlet port 134. The inlet 128 and outlet 132 passages are in fluid communication with tubing 18.

The inlet port 130 is located generally along the centerline of well 126. The outlet port 134 is radially spaced a selected distance from the inlet port 130. An elastomeric seal member 138 occupies the well 126. The seal member 138 includes first 140 and second 142 apertures which extend through the body of seal member 138. When the seal member 138 is properly positioned in well 126, the first aperture 140 registers with the inlet port 130 and the second aperture 142 registers with the outlet port 134. A pair of locating pins 146 are positioned in well 126 which mate with a pair of locating holes 148 in seal member 138 to align and retain the seal member 138 in the desired position in well 126.

The selector member 124 is rotatable on the base member 122 about an axis generally aligned with the centerline of well 126. The selector member 124 can be rotatably attached to the base member 122 by various means, such as by rotatably affixing by snap-fit engagement between a circumferential flange 120 on the selector member 124 and a mating circumferential ridge 152 on the base member 122.

The flow restrictor wafer 70 is carried by the selector member 124. More particularly, projecting ridges 154 formed within the inner wall of selector member 124 define a space generally corresponding to the shape of wafer 70. The wafer 70 is carried within this space with the ridges 154 contacting the peripheral edges of wafer 70 and preventing lateral movement of wafer 70.

As such, the wafer inlet 108 is in alignment with the inlet port 130 of base member 122 via the first aperture 140 in seal member 138. As the wafer 70 is carried for movement in common with the selector member 124, the inlet 108 of wafer 70 stays in alignment with the inlet port 130. This rotation also serves to place the various outlets 110, 112, 114, 116 of wafer 70 into and out of alignment with the outlet port 134 of base member 122 via the second aperture 142 in seal member 138, depending on the position of the selector member 124 within its circular path. As such, different flow rates can be selected in this embodiment by simply rotating the selector member 124.

Referring now back to FIG. 1, the means 14 for providing a controlled bolus dose of the fluid is seen. Such controlled bolus dose means is shown in U.S. application Ser. No. 308,972 to Winchell et al. which is assigned to the assignee of the present invention and which disclosure is incorporated herein.

The preferred embodiment of the controlled bolus dose means 14 includes a bolus dose apparatus 115 which includes housing 160 which can be worn in the same manner as a wristwatch. The housing 160 can include wristband portions 162 secured to the housing 160 by mounting pins 164 to which the wristband portions 162 are secured.

Figure 9:
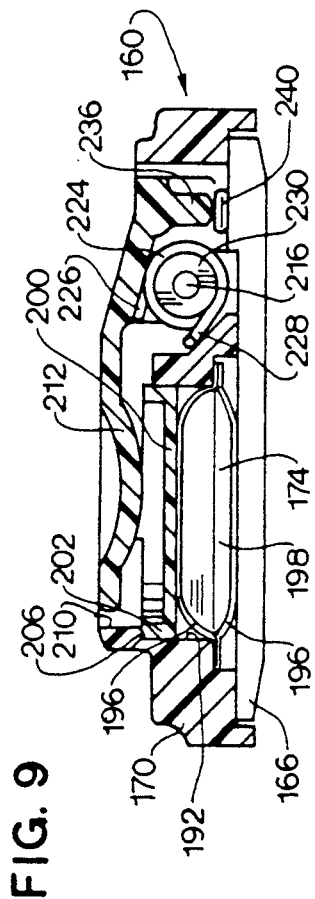
FIG. 9 is a cross-sectional view of an alternative preferred embodiment of the bolus means.
Figure 8:
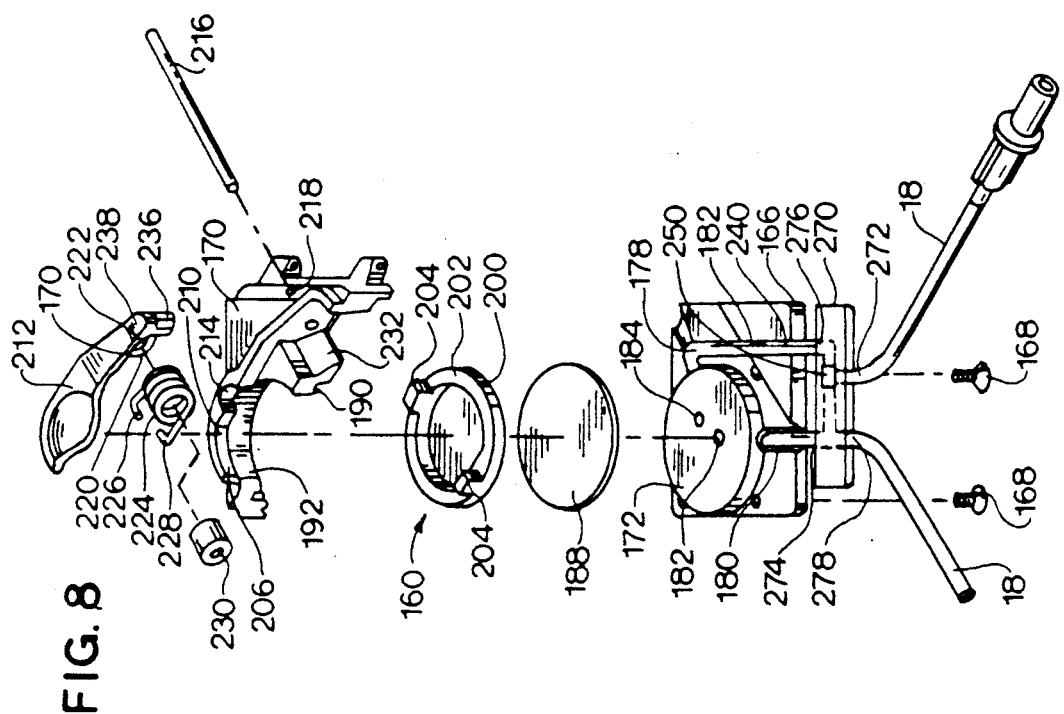
FIG. 8 is an exploded, partially cut-away perspective view of a preferred embodiment of the bolus means of FIG. 1.

Referring now to FIGS. 8 and 9, the housing 160 of bolus dose apparatus 15 is seen in detail. The housing 160 includes a back plate 166 secured by securing means such as screws 168 to a casing 170. Alternatively, the back plate 166 can be permanently secured by means such as sonic welding. A portion of back plate 166 can include a raised plateau 172 that forms one wall of a dose reservoir 174. A dose reservoir inlet 176 and a dose reservoir outlet 178 are formed within back plate 166. The inlet 176 includes a channel portion 180 and a bore portion 182 in fluid communication with the channel portion 180 and the interior of dose reservoir 174. The upstream tubing 18 is secured into the bore portion 180 by means such as friction fit or solvent bonding. The channel portion serves as a track to trap the conduit in a fixed location when the back plate 166 is secured to the casing 170.

The dose reservoir outlet 178 includes an outlet channel portion 182 and an outlet bore portion 184 in fluid communication with the interior of dose reservoir 174 and outlet channel portion 182. The downstream tubing 18 is secured to the outlet bore 182 by means such as a friction fit or solvent bonding.

The dose reservoir 174 includes an enclosed flexible container which can be compressed to force expulsion of the contents of dose reservoir 174. In one embodiment, this dose reservoir 174 can be a circular flexible sheet 188 placed on top of raised plateau 172 of back plate 166. The periphery of circular flexible sheet 188 rests on the periphery of raised plateau 172. The circular flexible sheet 188 may be made of, for example, polyisoprene rubber material.

The dose reservoir 174 can be formed by utilizing a pressure seal structure in the housing to press the flexible sheet 188 adjacent to its outer periphery against the raised plateau 172 creating a fluid tight seal between the flexible sheet 188 and the plateau 172. More particularly, the casing 170 can include a downwardly extending annular rib 190 disposed below and outwardly of a guide bore 192 so that the annular rib 190 is directly above the periphery of flexible sheet 188 and raised plateau 172. When the back plate 166 is secured to the casing 170 such as with the screws or sonic welding, the periphery of flexible sheet 188 is trapped between the annular rib 190 and the raised plateau 172.

In an alternative embodiment, seen in FIG. 9, the dose reservoir 174 ca include two flexible sheets 196 sealed together about the outer periphery of each to define a pillow 198. This pillow 198 is the enclosed flexible container contained in casing 170. The two flexible sheets 196 can be made of, for example, vinyl. The outer periphery seal includes apertures through which the upstream and downstream tubing extends to establish fluid communication with the inside of pillow 198. In this alternative embodiment, the back plate 166 need not include a raised plateau.

The control means of the apparatus includes dose reservoir compression means which in a preferred embodiment includes a floating plate 200 that rests on top of flexible sheet 188 or pillow 198 and has a diameter less than the diameter of guide bore 192. The floating plate 200 can include an upper annular ridge 202 projecting from the top side of floating plate 200 at its periphery. The floating plate 200 can further include two volume indicator pegs 204 projecting from the upper annular ridge 202.

A casing ridge 206 projects inwardly from the guide bore 192 at the top of guide bore 192 and acts as a stop that is part of the dose compression means. The floating plate 200 travels in a direction perpendicular to the back plate 166, the stop serving as an upper limit for the floating plate 200 when the upper annular ridge 202 thereof engage the stop.

The casing 170 defines an opening 210 for the control switch 212. Part of opening 210 is directly above the guide bore 192 and the floating plate 200. The defined opening 210 of casing 170 includes slots 214 in which the volume indicator pegs 204 of floating plate 200 travel as the floating plate 200 reaches its upper limit.

The control switch 212 is rotatably mounted upon a cylindrical pin 216 mounted in receiving sockets 218 within casing 170. The control switch 212 includes two mounting flanges 220 each having a pin opening 222 through which the pin 216 extends.

The control switch 212 rotates within a narrow arc about the axis of pin 216. A coil-type spring 224 is also mounted about the pin 216 between the mounting flanges 220. The pin 216 extends through the inside of coil-type spring 224. The spring 224 includes contact ends 226, 228. A spacer 230 is mounted on the pin 216 between the coil-type spring 224 and the pin 216. The contact ends 226, 228 tend to move circumferentially relative to the axis of pin 216 and the axis of coil-type spring 224.

The contact end 226 contacts and urges against the underside of control switch 212. The second contact end 228 contacts and urges against a shelf 232 in casing 170. The coil-type spring 224 thus serves as biasing means of the apparatus.

The control switch 212 can also include a blunt end conduit occlusion bar 236 made integrally with the control switch 212 and forming a single rigid part. The conduit occlusion bar 236 depends downwardly from the valve end 238 of control switch 212. The conduit occlusion bar 236 acts with the flexible wall portion 240 of downstream tubing 18 to form valve means for the apparatus.

Figure 10:
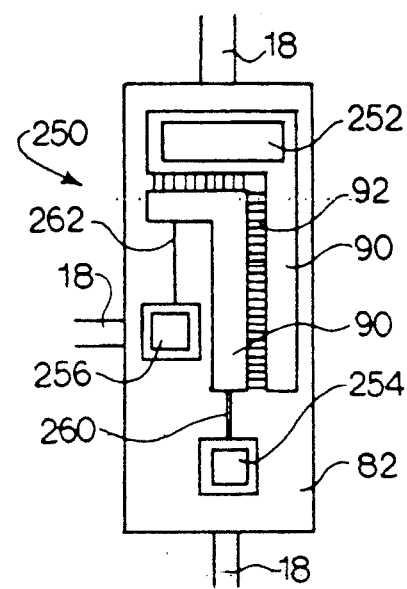
FIG. 10 is an enlarged overview of an alternative preferred embodiment of a flow rate wafer of the present invention.

Referring now to FIG. 10, another alternative preferred embodiment of the flow rate wafer is seen. This alternative embodiment is referred to herein as a dual wafer 250. This embodiment includes a wafer inlet 252, a continuous flow outlet 254, and a bolus flow outlet 256. The wafer 250 can include a fluid manifold 90 formed in association with the wafer inlet 252. In addition, a filtration area 92 can also be provided in association with the wafer inlet 252.

The wafer inlet 252, fluid manifold 90, and filtration area 92 are in fluid communication with both a continuous restrictor path 260 and a bolus restrictor path 262. The restrictor paths 260, 262 are formed with a preselected cross-sectional area and length to provide different restriction to flow. Fluid transversing the two flow paths 260, 262 will therefore flow at different preselected flow rates. The continuous restrictor path 260 is in fluid communication with the continuous flow outlet 254 while the bolus restrictor path 262 is in fluid communication with the bolus flow outlet 256.

Referring back to FIG. 8, housing 270 for the dual wafer 250 of FIG. 10 is seen in conjunction with the housing 160 of bolus dose apparatus 15. The housing 270 includes two inlet ports 272, 274 and two outlet ports 276, 278. The first housing inlet port 272 is in fluid communication with the means for providing a source of fluid under pressure 12 by means of tubing 18. The first housing inlet port 272 is thus connected to tubing 18 by means such as an adhesive. The first housing inlet port 272 is in fluid communication with the dual wafer inlet 252. As such, fluid enters the housing 270 through the first housing inlet port 272 and then flows through the dual wafer inlet 252 to the fluid manifold 90 of dual wafer 250. After flowing through the filtration area 92, the fluid flows in parallel through the continuous restrictor path 260 and the bolus restrictor path 262.

The first housing outlet 276 is in fluid communication with the bolus flow outlet 256 of dual wafer 250. The first housing outlet 276 is also in fluid communication with the input of bolus dose apparatus 15 by means such as tubing 18. The second housing input 274 is in fluid communication with the outlet of bolus dose apparatus 15. The second housing outlet 278 is in fluid communication with both the continuous flow outlet 254 of dual wafer 250 and the second housing input 274. The second housing outlet 278 is also in fluid communication with downstream tubing 18. The continuous fluid flow passes through the continuous restrictor path 260 to the second housing outlet 278. The bolus fluid flow passes through the bolus restrictor path 262 to the bolus dose apparatus 15, then from the bolus dose apparatus 15 to the housing second input 274, and then to the housing second outlet 278.

Referring again to FIG. 1, the operation of the device will be described. As previously seen, the means for providing a source of fluid under pressure 12 can preferably provide the fluid or beneficial agent at a pressure of about eight PSI. In one embodiment, this beneficial agent under the flow rate pressure is split into two flow paths by a Y-connector 48. The two flow paths are a continuous flow path 290 and a bolus flow path 292. The continuous flow path 290 leads to a constant flow regulator means 16. The bolus flow path 292 leads to a bolus flow regulator means 300 which in the preferred embodiment can include the same type flow restrictor as the constant flow regulator means 16, be it the glass capillary type, the wafer type, or the multi-channel adjustable wafer type.

In the alternative embodiment, the means for providing a source of fluid under pressure 12 is provided to the inlet 252 of dual wafer 250. The continuous flow path 290 is thus formed by the continuous restrictor path 260 while the bolus flow path 292 is formed by the bolus restrictor path 262.

The means for providing a source of fluid under pressure 12 and tubing 18 up to the two flow regulators define an approximate closed pressure system. This is because the flow rate through the flow restrictors is sufficiently small to maintain the closed pressure system at about eight PSI. As such, the fluid pressure at the inlet of the fluid flow restrictors of the present device remains at about eight PSI. It has been found that by keeping a closed pressure system and utilizing two flow restrictors in such parallel arrangement, no lag time is experienced. Lag time is that amount of time needed in series flow restrictors to replenish the pressure upstream of the constant flow restrictor after a bolus dose is administered.

In the continuous flow path 290, the flow rate pressure is supplied to the constant flow regulator means 16. The beneficial agent then flows through the constant flow regulator means 16 which governs the rate of flow of the fluid. In a preferred example, the continuous flow rate is set at about 0.5 ml per hour of the beneficial agent as determined by the length and diameter of the capillary bore.

From the outlet passage of the constant flow regulator means 16, in the first embodiment, tubing 18 is connected in direct fluid communication with a downstream Luer 308 by means such as, for example, a second Y-connector 306. In the alternative embodiment, the second housing outlet 278 of dual wafer housing 270 is directly connected to the downstream Luer 308 as a Y-type configuration is built into the housing 270. The downstream Luer 308 is adapted to be connected to a catheter for introduction into a patient's vein.

The bolus flow path 292 is also supplied to the bolus dose means 14 by an inlet passage of a bolus flow regulator means 300. In this second flow regulator means, the flow regulator sets the rate at which the bolus means dose reservoir 174 fills with fluid. In a preferred example, the bolus flow regulator means 300 is set at about 2.0 ml per hour. This rate plus the continuous flow rate represents the total discrete dose amount volume limit above which the patient will no be able to receive the beneficial agent. In the preferred example, the total discrete amount is about 2.5 ml per hour.

The outlet passage of bolus flow regulator means 300 is connected to the inlet passage of bolus dose apparatus 15 by means such as tubing 18. Thus, the bolus flow regulator means 300 and the bolus dose apparatus 15 form the means for providing a controlled bolus dose of the fluid 14. The bolus flow rate fills the dose reservoir 174 to its maximum volume as defined and limited by the floating plate and the stop, which in a preferred example is approximately 0.5 ml. This maximum volume represents the bolus dose discrete dose limit. The bolus flow rate expands the dose reservoir 174, over time in a linear manner to the maximum volume. As such, if the bolus dose is administered prior to the filling of dose reservoir 174, the amount of bolus dose administered is a linear function of the amount of time which has passed since the last bolus dose up to the time when the dose reservoir 174 is filled to its maximum volume thus attaining the bolus dose discrete dose limit.

The spring 224 biases the valve end of control switch 212, including the conduit occlusion bar 236, downwardly. The spring 224 also biases the end opposite the valve end of control switch 212 upwardly so that the control switch 212, although remaining within the defined opening of casing 270, is spaced from the floating plate 200. The flexible wall portion 240 of the downstream apparatus conduit is disposed directly underneath the conduit occlusion bar 236.

To activate the controlled bolus means dose, the patient pushes the upwardly biased end of control switch 212. This causes the control switch 212 end to contact the floating plate 200 and depress it downwardly out of engagement with the stop and compress the dose reservoir 174 by urging the flexible sheet 188 against the raised plateau 172 or the pillow 198 against the back plate 166. Before contact between the upwardly biased end of control switch 212 and floating plate 200 is made, the biasing force provided by the spring 126 is overcome by the force of the control switch 212 activation, lifting the valve end and the conduit occlusion bar 236 out of engagement with the flexible wall portion 240 of the downstream conduit thus placing the valve means in an open, operating mode.

As the floating plate 200 is urged downwardly by the control means, the dose of beneficial agent within dose reservoir 174 is expressed out of the dose reservoir 174, through the outlet. In one embodiment, the outlet is connected to downstream tubing which is connected to the second Y-connector 306 to establish direct fluid communication with the downstream Luer 308 and catheter. In a second embodiment, the outlet is connected to the dual wafer second housing input 274 which acts as the Y-connector and is in fluid communication with to the downstream Luer 308.

After the control switch 212 has been released by the patient, the flexible wall portion 240 of the downstream apparatus conduit is once again occluded by the blunt-ended conduit occlusion bar 236, thus placing the valve means in the closed mode of operation. In addition, the biasing spring 224 has returned the button end of the control switch to its inactivated, upper position. In this state, the floating plate 200 can be urged upwardly by the pressure of liquid entering the dose reservoir 174 until the upper annular ridge 202 of floating plate 200 engage the stop.

As such, the patient can supplement the continuous dose rate by activating the bolus dose apparatus 15. If the dose reservoir 174 is full, the patient will receive a full dose of the beneficial agent. If, however, the patient activates the bolus dose apparatus 15 prior to the time required to fill the dose reservoir 174, the patient will receive a fraction of a dose. Because the dose reservoir 174 fills only at the bolus rate selected via the bolus flow restrictor means 300, this fraction is a linear function of the amount of time passed since the last bolus activation, up to the maximum bolus amount of dose reservoir 174.

It should be understood that various changes and modifications to the preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

What is claimed is:

1. An apparatus for dispensing a fluid comprising:
mechanical means for providing a source of fluid under pressure;
regulating means in fluid communication with the pressurized source of fluid for providing a constant flow rate of the fluid;
bolus dose means having a dose reservoir in fluid communication with the pressured source of fluid, the dose reservoir having an upper volume limit which represents the discrete dose limit of the bolus dose means, and a control means for manually expressing the fluid in the dose reservoir from the dose reservoir; and
downstream tubing means in fluid communication with the regulating means and the dose reservoir such that the regulating means provides a constant maintenance flow of the fluid to the downstream tubing means while the bolus dose means provides a manually controllable bolus dose of the fluid to the downstream tubing means/

2. The apparatus of claim 1 wherein the regulating means includes a flow regulator.

3. The apparatus of claim 1 wherein the means for providing a source of fluid comprises:
an elastomeric bladder being capable of retaining fluid therein;
an housing containing the elastomeric bladder; and
tubing having a proximal end in fluid communication with the elastomeric bladder and a distal end in fluid communication with both the regulating means and the bolus dose means.

4. The apparatus of claim 1 wherein the bolus dose means further includes means in fluid communication with the means for providing a source of fluid and the dose reservoir for regulating the flow of fluid to the dose reservoir at the constant flow rate up to the discrete dose limit of the bolus means.

5. The apparatus of claim 4 wherein the regulating means also includes a flow regulator.

6. The apparatus of claim 5 wherein the flow regulator of the bolus dose means and the flow regulator of the regulating means are in parallel.

7. The apparatus of claim 5 wherein the flow regulator of the bolus means and the flow regulator of the regulating means are contained on a single wafer.

8. The apparatus of claim 5 wherein the means for providing a source of fluid under pressure and the tubing means upstream of the flow regulators of the regulating means and the bolus dose means are an approximate closed pressure system.

9. An apparatus for dispensing a beneficial agent to a patient comprising:

an elastomeric bladder capable of retaining the beneficial agent therein to create a pressurized source of the beneficial agent.
flow regulating means in fluid communications with the pressurized source of the beneficial agent;
a dose reservoir also in fluid communication with the pressurized source of the beneficial agent, the dose reservoir having valve means for preventing downstream flow of the beneficial agent and an upper volume limit;
control means for opening the valve means and expressing the beneficial agent from the dose reservoir; and
downstream tubing means in fluid communications with the flow regulating means and the dose reservoir such that the regulating means provides a constant maintenance flow of the beneficial agent to the downstream tubing means while the dose reservoir and the control means provide a bolus dose of the beneficial agent to the downstream tubing means.

10. The apparatus of claim 9 wherein the elastomeric bladder is contained in a housing and includes means for accepting fluid under pressure.

11. The apparatus of claim 9 further including a flow regulator in fluid communication with the pressurized source of the beneficial agent and the dose reservoir.

12. The apparatus of claim 11 wherein the flow regulating means and the flow regulator are in parallel.

13. The apparatus of claim 11 wherein the flow regulating means and the flow regulator are in the same housing.

14. The apparatus of claim 9 wherein the dose reservoir has an upper volume limit which represents the discrete dose limit of the dose reservoir.

15. An apparatus adapted to be connected to a source of pressurized beneficial fluid for delivery of the beneficial fluid to a patient comprising:
upstream tubing adapted to establish fluid communications with the source of pressurized beneficial fluid;
a flow regulator in fluid communication with the upstream tubing and a downstream tubing, the downstream tubing adapted for connection to the patient; and
bolus dose means having a dose reservoir in fluid communications with the upstream tubing, the dose reservoir having an upper volume limit which represents the discrete dose limit of the bolus dose means and a control means for providing a controllable bolus dose of the beneficial agent to the downstream tubing, the bolus dose means being in parallel with the flow regulator.

* * * * *